US010288628B2

(12) United States Patent
Ledden

(10) Patent No.: US 10,288,628 B2
(45) Date of Patent: May 14, 2019

(54) SPECTROSCOPIC METHODS FOR THE DETECTION OF GLYCATED HEMOGLOBIN

(71) Applicant: Siemens Healthcare Diagnostics Inc., Tarrytown, NY (US)

(72) Inventor: David J. Ledden, Medway, MA (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 177 days.

(21) Appl. No.: 15/302,674

(22) PCT Filed: Apr. 10, 2015

(86) PCT No.: PCT/US2015/025367
§ 371 (c)(1),
(2) Date: Oct. 7, 2016

(87) PCT Pub. No.: WO2015/157669
PCT Pub. Date: Oct. 15, 2015

(65) Prior Publication Data
US 2017/0030932 A1 Feb. 2, 2017

Related U.S. Application Data

(60) Provisional application No. 61/978,416, filed on Apr. 11, 2014.

(51) Int. Cl.
*B01L 3/00* (2006.01)
*G01N 33/52* (2006.01)
(Continued)

(52) U.S. Cl.
CPC ...... *G01N 33/723* (2013.01); *B01L 3/502753* (2013.01); *G01N 33/491* (2013.01); *G01N 33/52* (2013.01); *G01N 33/721* (2013.01);

*B01L 2200/0668* (2013.01); *B01L 2200/10* (2013.01); *B01L 2300/0627* (2013.01);
(Continued)

(58) Field of Classification Search
CPC ........ B01L 2200/0668; B01L 2200/10; B01L 2300/0627; B01L 2300/0681; B01L 2300/087; B01L 3/502753; G01N 33/49; G01N 33/491; G01N 33/492; G01N 33/52;
(Continued)

(56) References Cited

U.S. PATENT DOCUMENTS 6,027,692 A 2/2000 Galen et al.
6,054,039 A 4/2000 Shieh
(Continued)

FOREIGN PATENT DOCUMENTS

WO 02061436 A1 8/2002
WO 2005119211 A1 12/2005
(Continued)

OTHER PUBLICATIONS

Supplementary Partial European Search Report of European Application No. 15776237.8 dated Mar. 22, 2017.
(Continued)

*Primary Examiner* — Maureen Wallenhorst
(74) *Attorney, Agent, or Firm* — Kyle D. Petaja

(57) ABSTRACT

Kits, microfluidics devices, and assays for use in methods of spectroscopically determining a ratio of glycated hemoglobin to total hemoglobin in a whole blood sample are disclosed.

7 Claims, 2 Drawing Sheets

(51) Int. Cl.
*G01N 33/72* (2006.01)
*G01N 33/49* (2006.01)

(52) U.S. Cl.
CPC . *B01L 2300/0681* (2013.01); *B01L 2300/087* (2013.01); *Y10T 436/255* (2015.01)

(58) Field of Classification Search
CPC .... G01N 33/72; G01N 33/721; G01N 33/723; Y10T 436/25375; Y10T 436/255
USPC ..... 436/63, 66, 67, 164, 165, 169, 170, 177, 436/178; 422/420, 421, 73, 82.05, 82.09, 422/502, 503, 535
See application file for complete search history.

(56) References Cited

U.S. PATENT DOCUMENTS

| | | | |
|---|---|---|---|
| 6,399,293 B1* | 6/2002 | Pachl | G01N 33/558 422/550 |
| 6,677,158 B2* | 1/2004 | Hud | G01N 33/723 422/400 |
| 7,109,038 B2 | 9/2006 | Scholl et al. | |
| 7,356,521 B2 | 4/2008 | Wang et al. | |
| 7,670,853 B2* | 3/2010 | Jina | G01N 33/558 435/287.1 |
| 8,093,057 B2* | 1/2012 | Choi | G01N 33/726 422/400 |
| 8,557,590 B2* | 10/2013 | Bae | G01N 33/723 435/287.2 |
| 8,846,380 B2* | 9/2014 | Bae | B01L 3/502 435/287.1 |
| 2002/0164811 A1* | 11/2002 | Hud | G01N 33/723 436/67 |
| 2002/0173044 A1 | 11/2002 | Pachl et al. | |
| 2003/0068830 A1* | 4/2003 | McCroskey | G01N 33/68 436/518 |
| 2004/0089616 A1 | 5/2004 | Kellogg et al. | |
| 2005/0136551 A1 | 6/2005 | Mpock | |
| 2008/0108144 A1 | 5/2008 | Alam et al. | |
| 2010/0105020 A1 | 4/2010 | Schmidt et al. | |
| 2011/0117670 A1 | 5/2011 | Walker et al. | |
| 2011/0269147 A1 | 11/2011 | Chinnayelka | |
| 2012/0122139 A1 | 5/2012 | Park et al. | |
| 2013/0260387 A1 | 10/2013 | McCroskey et al. | |

FOREIGN PATENT DOCUMENTS

| | | | |
|---|---|---|---|
| WO | 2009067421 A1 | | 5/2009 |
| WO | 2011128702 A1 | | 10/2011 |
| WO | 2013078130 A1 | | 5/2013 |
| WO | 2014/033258 | * | 3/2014 |
| WO | 2014151450 A1 | | 9/2014 |

OTHER PUBLICATIONS

European Search Report and Written Opinion of European Application No. 15776237.8 dated Jul. 12, 2017.
International Search Report and Written Opinion of International Application No. PCT/US2015/025367 dated Jul. 7, 2015.
Flückiger et al., "Quantitation of Glycosylated Hemoglobin by Boronate Affinity Chromatography"; Jan. 1984; Diabetes 33(1): pp. 73-76.

* cited by examiner

SPECTROSCOPIC METHODS FOR THE DETECTION OF GLYCATED HEMOGLOBIN

CROSS REFERENCE TO RELATED APPLICATIONS/INCORPORATION BY REFERENCE STATEMENT

The subject application claims benefit under 35 USC § 119(e) of U.S. provisional Application No. 61/978,416, filed Apr. 11, 2014. The entire contents of the above-referenced patent application are hereby expressly incorporated herein by reference.

STATEMENT REGARDING FEDERALLY FUNDED RESEARCH OR DEVELOPMENT

Not Applicable.

BACKGROUND

Hemoglobin present in red blood cells can be glycated by the non-enzymatic addition of a glucose molecule to the amino terminus of the β-chain of the hemoglobin. Once a hemoglobin molecule is glycated, it remains glycated, and an accumulation of glycated hemoglobin within a red cell reflects the average level of glucose to which the cell has been exposed during its life cycle. The level of glycated hemoglobin present in an individual's blood is thus proportional to the level of glucose in the blood and is an indicator of the individual's mean daily blood glucose concentration over the previous four weeks to three months. The ratio of glycated hemoglobin to total hemoglobin in a whole blood sample is therefore quite useful in the diagnosis and monitoring of patients with diabetes mellitus.

Numerous methods exist for determining the level of glycated hemoglobin in human blood, most of which involve calculating the relative amount of glycated hemoglobin A (HbA1c) present in the blood, as hemoglobin A (HbA) is the major form of hemoglobin present in human blood. There are several methods currently used to detect HbA1c and Hb to determine glycemic control. Techniques such as high performance liquid chromatography and immunoaffinity selection are used in such methods, which take advantage of physical and/or chemical properties of glycated hemoglobin A that distinguish it from other forms of hemoglobin present in the blood. In the HPLC method, a whole blood sample is centrifuged, the cellular fraction lysed, and the hemoglobin fractions separated using an anion exchange HPLC column and an absorbance measurement. Other chromatographic methods like phenyl-boronate chromatography separation, where only HbA1c binds to the column and non-glycated Hb comes through, have also been used. Two other cartridge based methods use a combination of chemistries and/or immunoassays to measure Hb and HbA1c (e.g., DCA VANTAGE®, Siemens Healthcare Diagnostics Inc., Tarrytown, N.Y.; and AFINION™ HbA1c, Axis-Shield PoC AS, Oslo, Norway). In these cases, whole blood is lysed, and samples are reacted with a combination of dry and liquid reagents which are read spectrophotometrically.

However, the currently used methods require separation of the whole blood sample and detection of HbA1c and total hemoglobin in separate steps. Therefore, a need exists for new and improved assay methods for determining the ratio of glycated hemoglobin to total hemoglobin in a whole blood sample, as well as kits and microfluidics devices useful in said methods. It is to such assays that minimize sample processing, reduce the number of assay steps and reagents, and use a single technology to detect both HbA1c and Hb, as well as kits, devices, and methods related thereto, that the presently disclosed and/or claimed inventive concept(s) is directed.

DESCRIPTION OF THE SEVERAL VIEWS OF THE DRAWINGS

FIGS. 2A-C illustrate the use of the microfluidics device in a method of the presently disclosed and/or claimed inventive concept(s).

DETAILED DESCRIPTION

Figure 1:
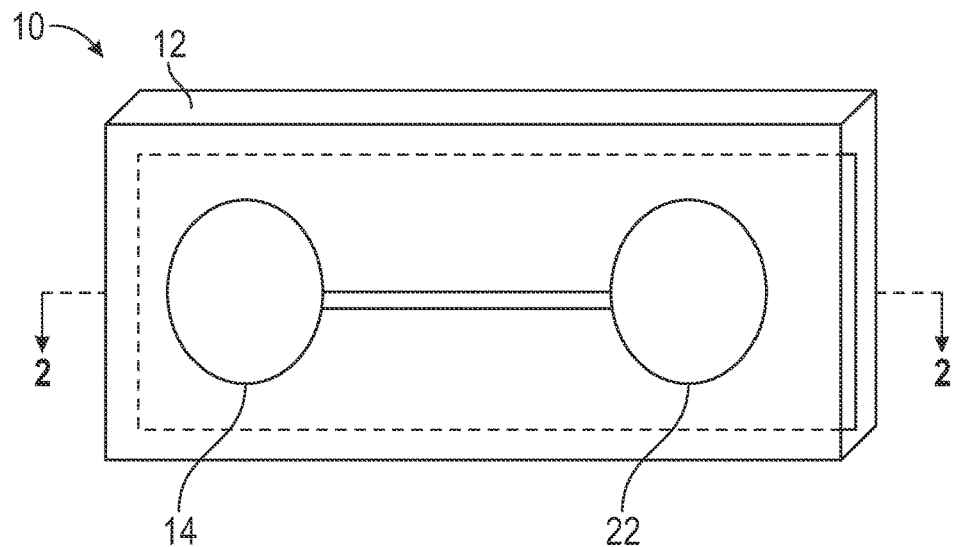
FIG. 1 is a perspective view of one embodiment of a microfluidics device architecture constructed in accordance with the presently disclosed and/or claimed inventive concept(s).

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well known and commonly used in the art.

All patents, published patent applications, and non-patent publications mentioned in the specification are indicative of the level of skill of those skilled in the art to which this presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and/or claimed herein can be made and executed without undue experimentation in light of the present disclosure. While the compositions and methods of this presently disclosed and/or claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and/or claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "purified" as used herein means at least one order of magnitude of purification is achieved compared to the starting material or of the natural material, for example but not by way of limitation, two, three, four or five orders of magnitude of purification of the starting material or of the natural material. Thus, the term "purified" as utilized herein does not necessarily mean that the material is 100% purified, and therefore such term does not exclude the presence of other material(s) present in the purified composition.

The term "sample" as used herein will be understood to include any type of biological sample that may be utilized in accordance with the presently disclosed and/or claimed inventive concept(s). Examples of biological samples that may be utilized include, but are not limited to, whole blood or any portion thereof (i.e., plasma or serum), saliva, sputum, cerebrospinal fluid (CSF), skin, interstitial fluid, tears, mucus, urine, swabs, combinations, and the like.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

Turning now to particular embodiments of the presently claimed and disclosed inventive concept(s), assay methods for determining the ratio of glycated hemoglobin to total hemoglobin in a whole blood sample, as well as compositions, kits, and microfluidics devices useful in said methods, are disclosed.

One embodiment of the presently disclosed and/or claimed inventive concept(s) is directed to kits useful for conveniently performing an assay for the determination of a ratio of glycated hemoglobin to total hemoglobin. The kit may contain any combination of the below-described components/reagents. In addition, the kit may further contain other component(s) and/or reagent(s) for conducting any of the particular assays described or otherwise contemplated herein. The nature of these additional reagent(s) will depend upon the particular assay format, and identification thereof is well within the skill of one of ordinary skill in the art.

The kits of the presently disclosed and/or claimed inventive concept(s) may include a blood separation membrane that traps red blood cells thereon and/or therein and allows plasma to pass therethrough. The kits may also include a waste collection material that is capable of being associated with the blood separation membrane and that is capable of wicking waste material away from the blood separation membrane and into the waste collection material.

The kits may further include a negatively charged surface that traps hemoglobin thereon and/or therein, while other components of lysed red blood cells are not trapped on the negatively charged surface. The negatively charged surface is capable of being subjected to spectroscopy to measure an amount of total hemoglobin trapped thereon and/or therein and an amount of glycated hemoglobin or non-glycated hemoglobin trapped thereon and/or therein. In certain embodiments, the negatively charged surface may be capable of being subjected to matrix-assisted laser desorption/ionization (MALDI) and/or surface-enhanced laser desorption/ionization (SELDI) time-of-flight (TOF) mass spectroscopy; in other embodiments, the negatively charged surface may be capable of being subjected to near-infrared (NIR), mid-infrared (MIR), and/or visible spectroscopy.

The kits may further include a waste collection material capable of being associated with the negatively charged surface and capable of wicking waste material away from the negatively charged surface and into the waste collection material.

Any separation membrane capable of trapping red blood cells thereon and/or therein and allowing plasma to pass therethrough may be utilized as the blood separation membrane. In one particular, non-limiting embodiment, the blood separation membrane is an asymmetric membrane vertical flow strip with larger pores on a first side and smaller pores on a second side. Non-limiting examples of materials from which the blood separation membrane may be constructed include small pore nitrocellulose, polysulfone membrane, polycarbonate, ceramic, glass fiber filter paper, combinations thereof, and the like. However, it is to be understood that the scope of the presently disclosed and/or claimed inventive concept(s) is not limited to the examples provided herein above. In addition, the choice of materials from which the blood separation membrane may be constructed is well within the skill of one of ordinary skill in the art, and thus no further description thereof is deemed necessary.

Any of the kits described above or otherwise contemplated herein may further include additional reagents/components, such as but not limited to, diluents, wash solutions (such as but not limited to, isotonic solutions), lysing agents (for lysing red blood cells), excipients (utilized for the reconstitution of lyophilized reagents), labeling agents, interference solutions, positive controls, negative controls, quality controls, and/or actuators, as well as any combination thereof. In addition, any of the compositions described herein above or otherwise contemplated herein may also include a microfluidics device in which one or more of the above-described components are provided.

One non-limiting example of an additional reagent that may be included in the kits of the presently disclosed and/or claimed inventive concept(s) is a labeling agent capable of labeling either glycated hemoglobin or non-glycated hemoglobin. The labeling agent may be added separately to the assay, or the labeling agent may be associated with another component/reagent of the kit, such as the negatively charged surface. Any labeling agent known in the art or otherwise contemplated herein that is capable of labeling either glycated hemoglobin or non-glycated hemoglobin and not disrupting the function of the blood separation membrane may be utilized in accordance with the presently disclosed and/or claimed inventive concept(s). One non-limiting example of a labeling agent that may be utilized is a boronate composition; boronate is capable of labeling glycated hemoglobin. In particular, the boronate may be labeled with a NIR/MIR dye.

In certain embodiments, the kits may further include an actuator for releasably advancing the blood separation membrane over the negatively charged surface.

The reagents of the compositions/kits/methods of the presently disclosed and/or claimed inventive concept(s) may be provided in any form and/or formulation that allow them to function in accordance with the presently disclosed and/or claimed inventive concept(s). For example but not by way of limitation, it may be desirable to provide the reagents in the form of single use reagents. In addition, it may be desirable to lyophilize one or more of the reagents; the use of dried reagents in microfluidics devices is described in detail in patent application publication WO 2013/078130 A1. Also, multiple components may be provided together in a single formulation and/or lyophilized in a single particle, if desired.

The components/reagents may each be provided in separate containers/compartments of the kits, or various components/reagents can be combined in one or more containers/compartments, depending on the competitive nature of the antibody binding constants/efficiencies and/or the stability of the components/reagents. The kits may further include other separately packaged reagents for conducting an assay, as described herein above. In addition, the kits may further include a microfluidics device in which the components/reagents are provided.

The relative amounts of the various components/reagents in the kits can vary widely to provide for concentrations of the components/reagents that substantially optimize the reactions that need to occur during the assay methods and further to optimize substantially the sensitivity of an assay. Under appropriate circumstances one or more of the components/reagents in the kit can be provided in a dry form, such as a lyophilized particle (including but not limited to, spheres, microtablets, powders, microspots, etc.), and the kit may further include excipient(s) for dissolution of the dried reagents; in this manner, a reagent solution having the appropriate concentrations for performing a method or assay in accordance with the presently disclosed and/or claimed inventive concept(s) can be obtained from these components.

The kits of the presently disclosed and/or claimed inventive concept(s) may further include a set of written instructions explaining how to use the kit. A kit of this nature can be used with any of the microfluidics devices and/or in any of the methods described or otherwise contemplated herein.

The presently disclosed and/or claimed inventive concept(s) is further directed to a microfluidics device in which the compositions/components described herein above are provided, wherein the microfluidics device may be used in determining a ratio of glycated hemoglobin to total hemoglobin. The microfluidics device may have one or more manual functions associated therewith (i.e., wherein pipetting is required for addition of one or more reagents and/or movement of a mixture between two compartments); alternatively, the microfluidics device may be a fully automatic, closed system in which the necessary reagents/components are provided in various compartments during construction of the microfluidics device (wherein the various compartments are in continuous fluidic communication (or are capable of being in continuous fluidic communication)), and thus no manual manipulation of the sample and/or reagent(s) is required for performance of the assay after the sample is added to the microfluidics device. The microfluidics device comprises one or more compartments containing the components described herein above; the microfluidics device may be provided with any number of compartments, any arrangement of compartments, and any distribution of the components there between, so long as the device is able to function in accordance with the presently disclosed and/or claimed inventive concept(s); non-limiting examples of device structure are provided herein below and in the Figures for illustrative purposes only. When provided with multiple compartments, the compartments may be completely separated from one another, or one or more compartments may be capable of being in fluidic communication with one another.

The microfluidics device may further include a sample application chamber and/or an inlet channel in which a sample may be applied. The sample application chamber/inlet channel may be capable of being in fluidic communication with the one or more compartments of the microfluidics device. In addition, when the microfluidics device is provided with both a sample application chamber and an inlet channel, the sample application chamber may be capable of being in fluidic communication with the inlet channel, while the inlet channel may be capable of being in fluidic communication with the one or more compartments in which the reagents are contained.

A sample may be applied directly in the compartment containing the blood separation membrane, or the sample may pass through the sample application chamber/inlet channel before entering the compartment(s) containing the assay reagent(s). When the sample passes through one or more components before reaching the assay compartment(s), substantially all of the sample may pass through and thus remain substantially intact upon reaching the assay compartment(s). Alternatively, only portions of the sample may reach the assay compartment. In one embodiment, this may occur simply because of size, weight, and/or volume restrictions in the compartments upstream of the assay compartment(s); in another embodiment, the microfluidics device may contain one or more structure(s) present in the sample application chamber, the inlet channel, a compartment upstream of the assay compartment(s), and/or any connection therebetween that allows for separation of certain components of a sample from a whole sample and/or delivery of said components to the assay compartment(s).

In certain embodiments, the microfluidics device includes a first compartment and a second compartment. The first compartment is capable of receiving a whole blood sample and may include the blood separation membrane (as described in detail herein above) and a waste collection material positioned below the blood separation membrane and associated therewith. As described herein above, the blood separation membrane traps red blood cells thereon and/or therein while allowing plasma to pass therethrough; in this manner, the plasma is wicked away from the blood separation membrane and into the waste collection material.

The second compartment includes a negatively charged surface (as described in detail herein above) and a waste collection material positioned therebelow and associated therewith. As described herein above, the negatively charged surface traps hemoglobin thereon and/or therein while allowing other components of lysed red blood cells to pass therethrough; in this manner, the other components of the lysed red blood cells are not trapped on the negatively charged surface and are wicked away from the negatively charged surface and into the waste collection material. In addition, the negatively charged surface is capable of being subjected to spectroscopy to measure: (1) an amount of total hemoglobin trapped thereon and/or therein, and (2) an amount of glycated hemoglobin or non-glycated hemoglobin trapped thereon and/or therein. The third compartment includes an optical read chamber that can be optically interrogated by a spectrometer.

The microfluidics device also includes an optical read chamber that is capable of being optically interrogated by a spectrometer. The optical read chamber may be associated with the first compartment or the second compartment, or the optical read chamber may be associated with another compartment (such as a third compartment).

The blood separation membrane is capable of releasable movement from association with the waste collection material to association with the negatively charged surface in the second compartment; for example but not by way of limitation, the blood separation membrane may be capable of releasable movement between the first and second compartments so that the blood separation membrane can be moved from association with the waste collection material to association with the negatively charged surface in the second compartment. In addition, the negatively charged surface is capable of releasable movement from association with the blood separation membrane to a position within the optical read chamber; for example but not by way of limitation, the negatively charged surface may be capable of releasable movement between the second compartment and the optical read chamber so that the negatively charged surface can be moved from association with the waste collection material to a position within the optical read chamber. In this manner, the negatively charged surface can be subjected to spectroscopy within the optical read chamber for measuring (1) an amount of total hemoglobin present on the negatively charged surface, and (2) an amount of one of glycated hemoglobin or non-glycated hemoglobin present on the negatively charged surface. The negatively charged surface is capable of being subjected to matrix-assisted laser desorption/ionization (MALDI) and/or surface-enhanced laser desorption/ionization (SELDI) time-of-flight (TOF) mass spectroscopy within the optical read chamber.

In certain embodiments, the microfluidics device may include one or more actuators that are responsible for releasably moving the blood separation membrane and/or the negatively charged surface as described herein above. The actuator(s) may be manually and/or automatically actuated.

For example but not by way of limitation, the microfluidics device may include first and second actuators; the first actuator releasably moves the blood separation membrane from association with the waste collection material to association with the negatively charged surface in the second compartment. The second actuator releasably moves the negatively charged surface the negatively charged surface from association with the waste collection material to a position within the optical read chamber.

While releasable movement of certain components of the microfluidics device are described herein above, it will be understood that the actual portions of the microfluidics device that move may vary, so long as the associations described herein above are achieved. That is, while releasable movement of the blood separation membrane and the negatively charged surface is described herein above, it will be understood that one or both of the waste collection materials and/or the optical read chamber may in fact be the portions of the microfluidics device that are advancing/moving.

Any of the compartments of the microfluidics device may be sealed to maintain reagent(s) contained therein in a substantially air tight environment until use thereof; for example, compartments containing lyophilized reagent(s) may be sealed to prevent any unintentional reconstitution of the reagent(s). The inlet channel and a compartment, as well as two compartments, may be described as being "capable of being in fluidic communication" with one another; this phrase indicates that the compartment(s) may still be sealed, but the two compartments are capable of having fluid flow there between upon puncture of a seal formed therein or there between.

The microfluidics devices of the presently disclosed and/or claimed inventive concept(s) may be provided with any other desired features known in the art or otherwise contemplated herein. For example, but not by way of limitation, the microfluidics devices of the presently disclosed and/or claimed inventive concept(s) may further include one or more additional compartments containing other solutions, such as but not limited to, diluents, wash solutions, lysing agents (for lysing red blood cells), excipients (utilized for the reconstitution of lyophilized reagents), labeling agents, interference solutions, positive controls, negative controls, quality controls, and/or actuators, as well as any combination thereof. For example, the microfluidics device may include one or more additional compartments containing a diluent, and these additional compartment(s) may be capable of being in fluidic communication with any other compartment(s) of the device. In another example, the microfluidics device may further include one or more additional compartments containing at least one excipient for reconstitution of one or more lyophilized reagents, and the additional compartment(s) may be capable of being in fluidic communication with any other compartment(s)/channel(s) of the device (such as the compartment containing the lyophilized reagent). Further, the microfluidics device may include one or more additional compartments containing a wash solution, and the compartment(s) may be capable of being in fluidic communication with any other compartment(s)/channel(s) of the device.

In particular embodiments, the microfluidics device containing a first compartment, a second compartment, and an optical read chamber may contain a third compartment that is capable of being in fluidic communication with the inlet channel, the first compartment, the second compartment, and/or the optical read chamber. For example, the third compartment may contain a lysing agent and/or a wash solution and may be capable of being in fluidic communication with the inlet channel, the first compartment, the second compartment, and/or the optical read chamber. In another example, the third compartment may contain a labeling agent and be capable of being in fluidic communication with the inlet channel, the first compartment, the second compartment, and/or the optical read chamber. In yet further embodiments, the microfluidics device may include a combination of any of the above additional compartments.

Alternatively, when a labeling agent is required, the negatively charged surface has a labeling agent capable of labeling one of glycated hemoglobin or non-glycated hemoglobin associated therewith.

In addition, any of the kits/microfluidics devices described or otherwise contemplated herein may include multiple assays multiplexed in a single kit/device. When multiple assays are present, both of the assays may be constructed and function as described herein. Alternatively, an assay as described herein may be multiplexed with any other type of assay known in the art that is capable of being contained within the kits/microfluidics devices of the presently disclosed and/or claimed inventive concept(s). When multiple assays are present in a single kit/microfluidics device, the two or more assays may be run simultaneously and/or sequentially (including wholly or partially sequentially). When two or more assays are run simultaneously, it may be desired to utilize a detection reagent that is detected at a different mass (for MALDI/SELDI spectroscopy) and/or a different wavelength (for NIR/MIR/visible spectroscopy).

When multiple assays are present in a single microfluidics device, multiple inlet channels may be connected to the sample application chamber. In certain embodiments, a portion of the sample may be passed from the sample application chamber to the multiple inlet channels without regard for the content thereof. Alternatively, structure(s) may be present in the sample application chamber, the inlet channels, and/or the connection therebetween that allow for separation of certain components from the whole sample and delivery of said components to the different assays. A non-limiting example of a sample distribution device that may be utilized in accordance with the presently disclosed and/or claimed inventive concept(s) is described in detail in Provisional Application No. 61/790,580, filed Mar. 15, 2013, entitled "Microfluidic Distributing Device."

Certain embodiments of the presently disclosed and/or claimed inventive concept(s) are directed to a method of determining a ratio of glycated hemoglobin to total hemoglobin in a whole blood sample. In the method, a whole blood sample is applied to an upper surface of the blood separation membrane (as described herein above) of a microfluidics device. The blood separation membrane has a lower surface that is associated with a first waste collection material; incubation of the sample with the blood separation membrane results in the association/capture of red blood cells from the whole blood sample on and/or in the blood separation membrane, while plasma passes through the blood separation membrane and is wicked away from the blood separation membrane and into the first waste collection material. A portion of the microfluidics device is then moved so that the blood separation membrane is positioned over a negatively charged surface that has a second waste collection material positioned therebelow and in association therewith.

In one embodiment, a lysing agent is applied to the blood separation membrane and incubated therewith, resulting in lysing of the red blood cells associated with the blood separation membrane. During the incubation step, the contents of the lysed red blood cells pass through the blood separation membrane and are brought into contact with the negatively charged surface; the negatively charged surface traps hemoglobin thereon and/or therein, while the other components of lysed red blood cells are wicked away from the negatively charged surface and into the second waste collection material.

A portion of the microfluidics device is then moved so that the negatively charged surface is positioned within an optical read chamber that allows for optical interrogation of the negatively charged surface by a spectrometer. Two spectroscopic measurements are then obtained: (1) an amount of total hemoglobin on and/or in the negatively charged surface, and (2) an amount of one of glycated hemoglobin or non-glycated hemoglobin on and/or in the negatively charged surface. A ratio of glycated hemoglobin to total hemoglobin in the whole blood sample is then determined based on the spectroscopic measurements.

In certain particular, non-limiting embodiments, total hemoglobin may be spectroscopically measured by visible spectroscopy. Total hemoglobin concentration can be calculated using a number of wavelengths in the visible spectral range; for example, but not by way of limitation, total hemoglobin can be detected at wavelengths in a range of from about 350 nm to about 650 nm. Various methods of measuring total hemoglobin by visible spectroscopy are well known in the art, and the selection of a visible spectroscopic method for use in accordance with the presently disclosed and/or claimed inventive concept(s) is well within the skill of one of ordinary skill in the art; thus, no further description thereof is deemed necessary.

When the negatively charged surface is spectroscopically measured by near-infrared (NIR) and/or mid-infrared (MIR) spectroscopy, the method may further include the step of treating the negatively charged surface with a labeling agent capable of labeling one of glycated hemoglobin or non-glycated hemoglobin prior to positioning the negatively charged surface within the optical read chamber. The method may also include the step of washing the negatively charged surface after application of the labeling agent thereto and while the negatively charged surface is associated with the second waste collection material. Alternatively, the negatively charged surface may have a labeling agent associated therewith, wherein the labeling agent is capable of labeling one of glycated hemoglobin or non-glycated hemoglobin.

In another embodiment, the negatively charged surface is spectroscopically measured by matrix-assisted laser desorption/ionization (MALDI) and/or surface-enhanced laser desorption/ionization (SELDI) time-of-flight (TOF) mass spectroscopy.

The method may include any additional steps that increase the efficiency of determining the ratio of glycated hemoglobin to total hemoglobin. For example but not by way of limitation, the method may further include one or more wash steps, such as (1) washing the blood separation membrane after applying the whole blood sample thereto and while the blood separation membrane is associated with the first waste collection material, (2) washing the negatively charged surface after application of the lysing agent thereto and while the negatively charged surface is associated with the second waste collection material, and/or (3) washing the negatively charged surface after application of the labeling agent thereto and while the negatively charged surface is associated with the second waste collection material.

As mentioned above, the sample and various components of the method are provided in combination (either simultaneously or sequentially). When the sample and various components of the method are added sequentially, the order of addition of the sample/components may be varied; a person having ordinary skill in the art can determine the particular desired order of addition of the sample/different components to the assay. The simplest order of addition, of course, is to add all the materials simultaneously and determine the signal produced therefrom. Alternatively, the sample and each of the components, or groups of components, can be combined sequentially. In certain embodiments, an incubation step may be involved subsequent to addition of sample and/or each component.

Another embodiment of the presently disclosed and/or claimed inventive concept(s) is directed to a method of determining a ratio of glycated hemoglobin to total hemoglobin in a whole blood sample. In this method, a whole blood sample is applied to the upper surface of the blood separation membrane of the microfluidics device and incubated therewith, followed by application of a labeling agent to the blood separation membrane and incubation therewith; the labeling agent penetrates the red blood cells and labels either glycated hemoglobin or non-glycated hemoglobin. In addition, excess labeling agent that did not penetrate the red blood cells is wicked away from the blood separation membrane and into the waste collection material. A wash solution then may be applied to the blood separation membrane and incubated therewith, wherein the wash solution is wicked away from the blood separation membrane and into the waste collection material. An amount of total hemoglobin on the blood separation membrane and an amount of either (1) labeled glycated hemoglobin on the blood separation membrane, or (2) labeled non-glycated hemoglobin on the blood separation membrane is then measured via near-infrared (NIR), mid-infrared (MIR), and/or visible spectroscopy, and a ratio of glycated hemoglobin to total hemoglobin in the whole blood sample is determined based on the spectroscopic measurements.

The sample may be exposed to a separation step prior to combination with any of the assay reagents. For example but not by way of limitation, it may be desirable to separate the red blood cells from the whole blood sample prior to commencing the assay, so that components present in the whole blood sample do not affect the sensitivity, dynamic range, and/or detection limit of the assay.

In addition, it may be desired to dilute the mixture formed from during any of the incubation/binding steps prior to performing the spectroscopic measurements, and thus the method may further include the step of adding a diluent to the incubated mixture of sample and reagents.

Figure 2:
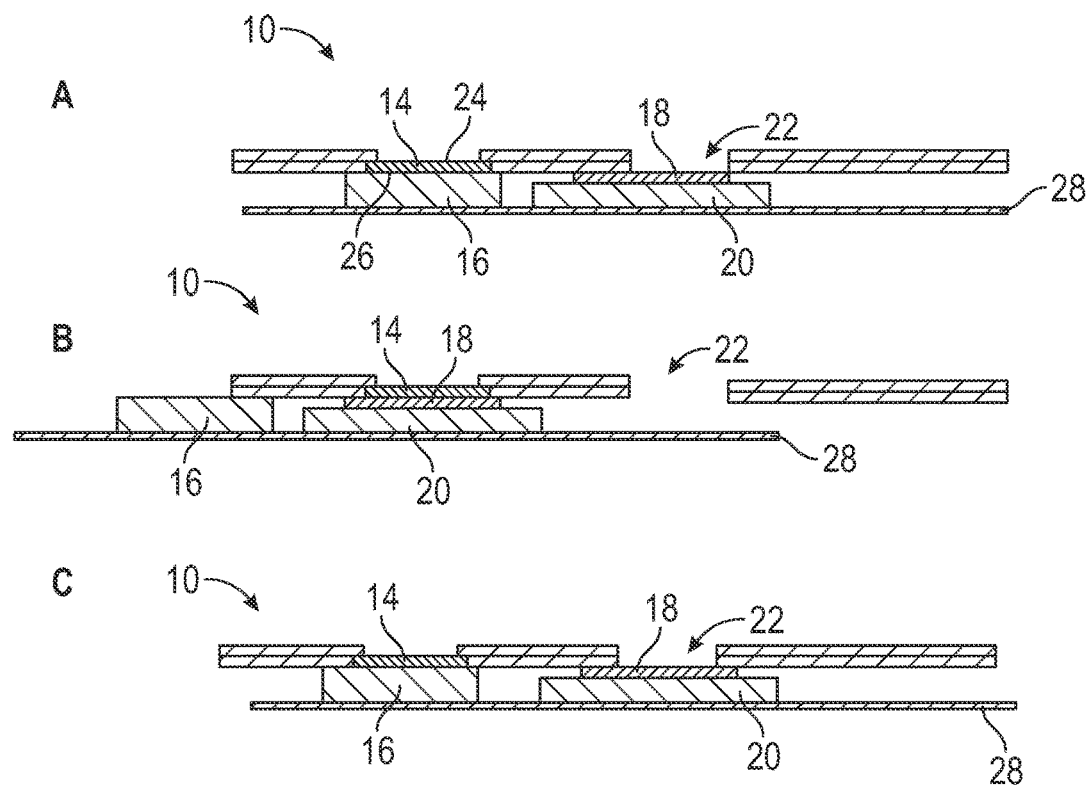
FIGS. 2A, 2B, and 2C are cross sectional views of the microfluidics device of FIG. 1 taken along line 2-2.

Turning now to the particular embodiments shown in the Drawings, FIGS. 1 and 2A-C illustrate one embodiment of a microfluidics device constructed in accordance with the presently disclosed and/or claimed inventive concept(s). The microfluidics device is indicated by the general reference numeral 10 and includes a housing 12; as shown in FIG. 2A, the housing 12 includes a blood separation membrane 14 and a waste collection material 16 associated therewith, a negatively charged surface 18 having a waste collection material 20 associated therewith, and an optical read chamber 22.

In use, a whole blood sample is applied to an upper surface 24 of the blood separation membrane 14 of the microfluidics device 10. A lower surface 26 of the blood separation membrane 14 is associated with the first waste collection material 16, whereby incubation of the whole blood sample with the blood separation membrane 14 results in the association/capture of red blood cells from the whole blood sample on and/or in the blood separation membrane 14, while plasma passes through the blood separation membrane 14 and is wicked away from the blood separation membrane 14 and into the first waste collection material 16. A portion of the microfluidics device 10 is then moved so that the blood separation membrane 14 is positioned over the negatively charged surface 18 that has the second waste collection material 20 positioned therebelow and in association therewith.

A portion of the microfluidics device 10 is then moved so that the negatively charged surface 18 is positioned within the optical read chamber 22 that allows for optical interrogation of the negatively charged surface 18 by a spectrometer, as described herein above. An amount of total hemoglobin on the negatively charged surface and an amount of either glycated hemoglobin or non-glycated hemoglobin is measured, so that a ratio of glycated hemoglobin to total hemoglobin in the whole blood sample can be determined based on the spectroscopic measurements.

Any portion/component of the microfluidics device 10 may be manually or automatically advanced to provide the releasable movements and associations described herein. In the particular embodiment shown in FIG. 2B, the blood separation membrane 14 is capable of releasable movement from association with the waste collection material 16 to association with the negatively charged surface 18. As shown in FIG. 2C, the negatively charged surface 18 is capable of releasable movement from association with the blood separation membrane 14 to a position within the optical read chamber 22. An actuator 28 is shown in FIGS. 2A-C as having the waste collection materials 16 and 20 associated therewith (and the negatively charged surface 18 indirectly associated therewith via the waste collection material 20); in this manner, the actuator 28 is responsible for advancing the waste collection material 16 and the negatively charged surface 18 having the waste collection material 20 associated therewith so that the waste collection material 16 is associated with the blood separation membrane 14 when needed, and the negatively charged surface 18 is associated with the blood separation membrane 14 when needed and positioned in the optical read chamber 22 when needed. However, the use of the actuator 28 is for purposes of example only, and other mechanisms of providing the releasable movements and associations described herein are also encompassed within the presently disclosed and/or claimed inventive concept(s).

Figure 3:
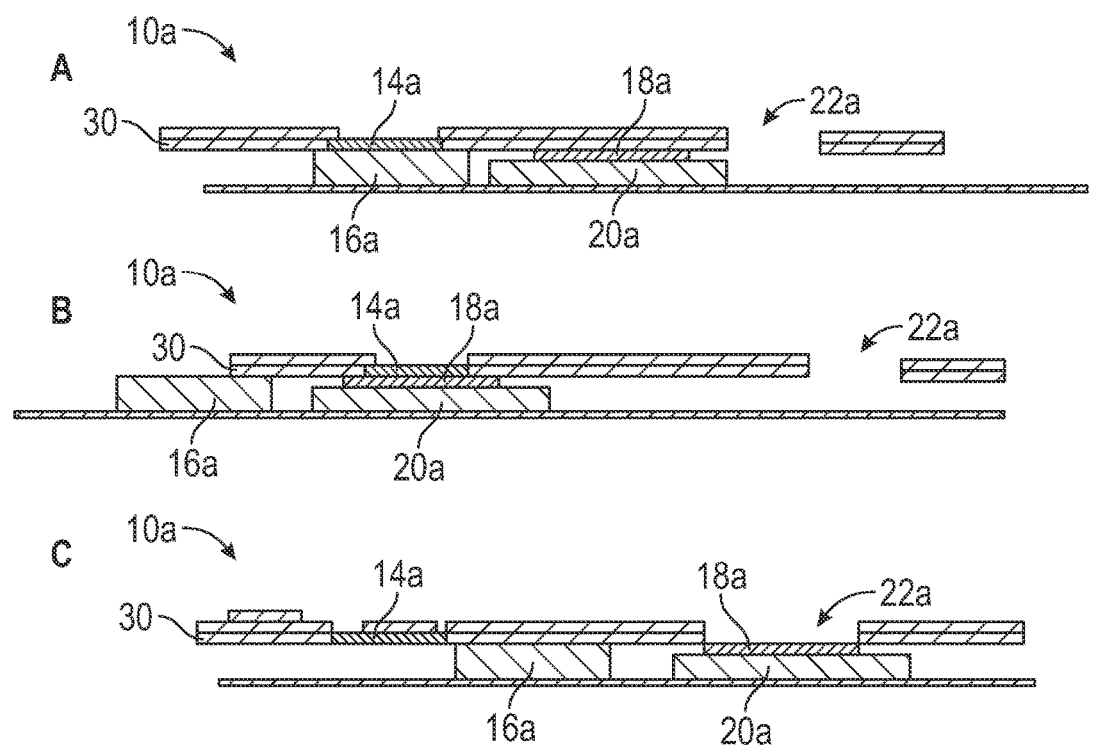
FIGS. 3A, 3B, and 3C are cross sectional views of another embodiment of microfluidics device architecture constructed in accordance with the presently disclosed and/or claimed inventive concept(s) and use thereof in a method as described herein.

For example, FIGS. 3A-C illustrate a microfluidics device 10a that is similar to the microfluidics device 10 of FIGS. 1 and 2A-C, except that the microfluidics device 10a contains a different actuation mechanism. As shown in FIG. 3A, the microfluidics device 10a includes a blood separation membrane 14a having a waste collection material 16a associated therewith, a negatively charged surface 18a having a waste collection material 20a associated therewith, and an optical read chamber 22a.

As shown in FIGS. 3B-C, an actuator 30 is associated with the blood separation membrane 14a and the optical read chamber 22a; in this manner, the actuator 30 is responsible for advancing the blood separation membrane 14a from association with the waste collection material 16a to association with the negatively charged surface 18a. The actuator 30 is also responsible for advancing the optical read chamber 22a to a position wherein the negatively charged surface 18a is positioned therewithin.

In addition, the presently disclosed and/or claimed inventive concept(s) includes the use of multiple actuators, each of which advances one or more components of the microfluidics device so that the releasable movements and associations described herein above can be achieved. For example, a microfluidics device constructed in accordance with the presently disclosed and/or claimed inventive concept(s) may include both an actuator similar to the actuator 28 of FIGS. 2A-C and an actuator similar to the actuator 30 of FIGS. 3A-C.

Figure 4:
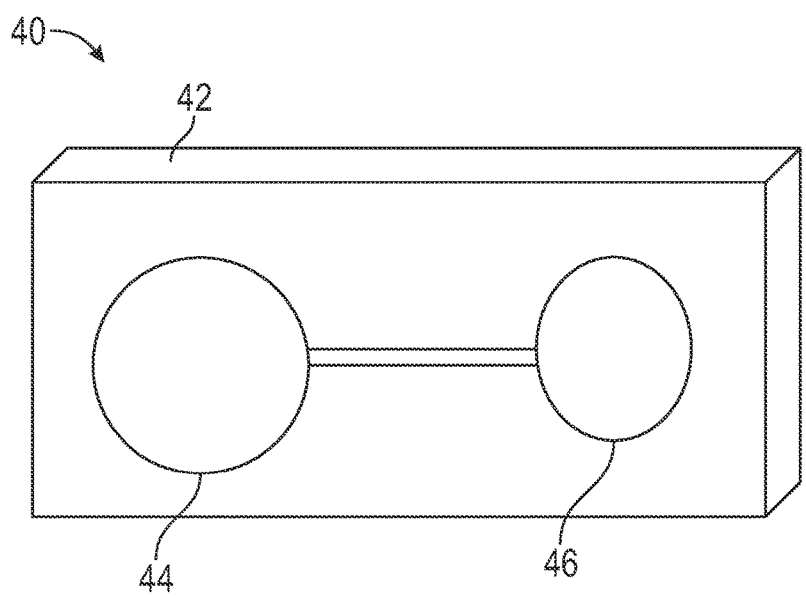
FIG. 4 is a perspective view of yet another embodiment of microfluidics device architecture constructed in accordance with the presently disclosed and/or claimed inventive concept(s).

FIG. 4 illustrates another embodiment of a microfluidics device 40 similar to the microfluidics device 10 of FIGS. 1 and 2A-C and the microfluidics device 10a of FIGS. 3A-C, except that a single component that functions as both blood separation membrane and negatively charged surface is utilized, and thus no actuation steps are performed in the microfluidics device 40. The microfluidics device 40 includes a housing 42 that contains a compartment 44 containing the blood separation membrane/negatively charged surface component; the housing also contains one or more compartments 46 that are capable of being in fluidic communication with the compartment 44. A whole blood sample may be applied to the compartment 44, and red blood cells in the whole blood sample are captured on and/or in the blood separation membrane/negatively charged surface, while plasma passes through the blood separation membrane/negatively charged surface and is wicked away from the blood separation membrane/negatively charged surface and into a waste collection material associated therewith that is also contained in the compartment 44.

A labeling agent may then be applied to the blood separation membrane/negatively charged surface; the labeling agent penetrates the red blood cells and labels either glycated hemoglobin or non-glycated hemoglobin. The labeling agent may be applied to the compartment 44 in a similar manner as the whole blood sample, or the labeling agent may be applied to the compartment 46 that is capable of being in fluidic communication with the compartment 44. Excess labeling agent that does not penetrate the red blood cells is wicked away from the blood separation membrane/negatively charged surface and into the waste collection material positioned in the compartment 44.

A wash solution may then be applied to the blood separation membrane/negatively charged surface. The wash solution may be applied to the compartment 44 in a similar manner as the whole blood sample and/or labeling agent, or the wash solution may be applied in the compartment 46 that is capable of being in fluidic communication with the compartment 44. The wash solution is wicked away from the blood separation membrane/negatively charged surface and into the waste collection material present in the compartment 44. The blood separation membrane/negatively charged surface may then be subjected to spectroscopy, such as but not limited to, near-infrared (NIR), mid-infrared (MIR), and/or visible spectroscopy, and an amount of total hemoglobin on the blood separation membrane/negatively charged surface and an amount of either (1) labeled glycated hemoglobin on the blood separation membrane/negatively charged surface, or (2) labeled non-glycated hemoglobin on the blood separation membrane/negatively charged surface is measured, so that a ratio of glycated hemoglobin to total hemoglobin in the whole blood sample can be determined based on the spectroscopic measurements.

It will be understood that the number of incubation/mixing compartments and order of application of the assay reagents within the open system microfluidics devices depicted in FIGS. 1-4 is for purposes of illustration only, and should not be construed as limiting. While FIGS. 1-4 depict microfluidics devices having one, two, or three incubation/mixing compartments in which the assay reagents are contained, it will be understood that devices having one, two, three, four, or more incubation/mixing compartments in which the assay reagents are contained are fully contemplated within the scope of the presently disclosed and/or claimed inventive concept(s). In addition, when the device contains two or more incubation/mixing compartments, the assay reagents may be dispersed between the two or more incubation/mixing compartments in any desired order, so long as the assay can function as described herein. Further, regardless of the number of incubation/mixing compartments present, the final incubation/mixing compartment may also be a read chamber; alternatively, a read chamber may also be present in the microfluidics device in addition to the one, two, three, or four incubation/mixing chambers. Also, the microfluidics device may further contain one or more additional structures, such as but not limited to, an additional compartment in which a lysing agent, labeling agent, wash solution, diluent, and/or excipient may be applied prior to addition to one or more of the compartments.

Any of the compartments of any of the microfluidics devices described or otherwise contemplated herein may be sealed to maintain reagent(s) contained therein in a substantially air tight and/or substantially light tight environment until use thereof; for example, compartments containing lyophilized reagent(s) may be sealed to prevent any unintentional reconstitution of the reagent and/or exposure of any of the reagents to light. The inlet channel and a first compartment, as well as two compartments, may be described as being "capable of fluidic communication" with one another; this phrase indicates that the compartment(s) may still be sealed, but are capable of having fluid flow there between upon puncture of a seal formed therein.

In addition, it is to be understood that any of the microfluidics devices described or otherwise contemplated herein may further be provided with additional chambers and/or other fluidic circuits. For example, but not by way of limitation, any of the microfluidics devices may additionally contain mixing chamber(s) and/or fluidic circuit(s) that are provided between two reagent chambers.

Thus, in accordance with the presently disclosed and/or claimed inventive concept(s), there have been provided kits, microfluidics devices, and assays for use in methods of spectroscopically determining a ratio of glycated hemoglobin to total hemoglobin that fully satisfy the objectives and advantages set forth hereinabove. Although the presently disclosed and/or claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and/or claimed inventive concept(s).

The following examples are provided for illustrative purposes only and are intended to be non-limiting examples only.

In a first illustrative example of a kit for determining a ratio of glycated hemoglobin to total hemoglobin, the kit comprises a blood separation membrane, wherein the blood separation membrane traps red blood cells thereon and/or therein, and wherein plasma passes through the blood separation membrane; a waste collection material capable of being associated with the blood separation membrane and capable of wicking waste material away from the blood separation membrane and into the waste collection material; a negatively charged surface, wherein the negatively charged surface traps hemoglobin thereon and/or therein, and wherein other components of lysed red blood cells are not trapped on the negatively charged surface, and wherein the negatively charged surface is capable of being subjected to spectroscopy to measure an amount of total hemoglobin trapped thereon and/or therein and an amount of glycated hemoglobin or non-glycated hemoglobin trapped thereon and/or therein; and a waste collection material capable of being associated with the negatively charged surface and capable of wicking waste material away from the negatively charged surface and into the waste collection material. In a second illustrative kit, the blood separation membrane is an asymmetric membrane vertical flow strip with larger pores on a first side and smaller pores on a second side. In a third illustrative kit, the kit further comprises a lysing agent capable of lysing the red blood cells. In a fourth illustrative kit, the kit further comprises an actuator for releasably advancing the blood separation membrane over the negatively charged surface. In a fifth illustrative kit, the negatively charged surface is capable of being subjected to at least one of near-infrared (NIR) spectroscopy, mid-infrared (MIR) spectroscopy, and visible spectroscopy. In a sixth illustrative kit, the fifth illustrative kid further comprises a labeling agent capable of labeling either glycated hemoglobin or non-glycated hemoglobin. In a seventh illustrative kit, the labeling agent of the fifth illustrative kit includes is associated with the negatively charged surface. In an eighth illustrative kit, the labeling agent of the sixth or seventh illustrative kits comprise boronate, wherein the boronate is capable of labeling glycated hemoglobin. In a ninth illustrative kit, the boronate of the eight illustrative kit is labeled with a NIR/MIR dye. In a tenth illustrative kit, the negatively charged surface is capable of being subjected to matrix-assisted laser desorption/ionization (MALDI) and/or surface-enhanced laser desorption/ionization (SELDI) time-of-flight (TOF) mass spectroscopy. In an eleventh illustrative kit, the kit further comprises a wash solution.

In a first illustrative example of a microfluidics device for determining a ratio of glycated hemoglobin to total hemoglobin, the microfluidics device comprises: a first compartment capable of receiving a whole blood sample, the at least one compartment comprising a blood separation membrane and a waste collection material positioned therebelow and associated therewith, wherein the blood separation membrane traps red blood cells thereon and/or therein, and wherein plasma passes through the blood separation membrane and is wicked away from the blood separation membrane and into the waste collection material; a second compartment comprising a negatively charged surface and a waste collection material positioned therebelow and associated therewith, wherein the negatively charged surface traps hemoglobin thereon and/or therein, and wherein other components of lysed red blood cells are not trapped on the negatively charged surface and are wicked away from the negatively charged surface and into the waste collection material, and wherein the negatively charged surface is capable of being subjected to spectroscopy to measure an amount of total hemoglobin trapped thereon and/or therein and an amount of glycated hemoglobin or non-glycated hemoglobin trapped thereon and/or therein; an optical read chamber capable of being optically interrogated by a spectrometer; wherein the blood separation membrane is capable of releasable movement from association with the waste collection material to association with the negatively charged surface in the second compartment; and wherein the negatively charged surface is capable of releasable movement from association with the blood separation membrane to a position within the optical read chamber, and wherein the negatively charged surface can be subjected to spectroscopy within the optical read chamber of the third compartment for measuring (1) an amount of total hemoglobin present on the negatively charged surface, and (2) an amount of one of glycated hemoglobin or non-glycated hemoglobin present on the negatively charged surface. In a second illustrative microfluidics device, the device further comprises a first actuator for releasably moving the blood separation membrane movement from association with the waste collection material to association with the negatively charged surface in the second compartment; and a second actuator for releasably moving the negatively charged surface from association with the waste collection material to a position within the optical read chamber. In a third illustrative microfluidics device, at least one of the first and second actuators of the second illustrative microfluidics device is manually actuated. In a fourth illustrative microfluidics device, at least one of the first and second actuators of the second illustrative microfluidics device is automatically actuated. In a fourth illustrative microfluidics device, the blood separation membrane is an asymmetric membrane vertical flow strip with larger pores on a first side and smaller pores on a second side. In a fifth illustrative microfluidics device, at least one additional compartment that is capable of being in fluidic communication with the first compartment and/or the second compartment, and wherein the at least one additional compartment contains a lysing agent capable of lysing red blood cells. In a sixth illustrative microfluidics device, the negatively charged surface is capable of being subjected to at least one of near-infrared (NIR) spectroscopy, mid-infrared (MIR) spectroscopy, and visible spectroscopy within the optical read chamber. In a seventh illustrative microfluidics device, the sixth illustrative kit further comprising at least one additional compartment that is capable of being in fluidic communication with the second compartment, and wherein the at least one additional compartment contains a labeling agent capable of labeling either glycated hemoglobin or non-glycated hemoglobin. In an eight illustrative microfluidics device, the negatively charged surface of the sixth illustrative device has a labeling agent capable of labeling one of glycated hemoglobin or non-glycated hemoglobin associated therewith. In a ninth illustrative microfluidics device, the labeling agent of the sixth or seventh illustrative device comprises boronate, wherein the boronate labels one of glycated hemoglobin or non-glycated hemoglobin on and/or in the negatively charged surface. In a tenth illustrative microfluidics device, the boronate in the ninth device is labeled with a NIR/MIR dye. In an eleventh third illustrative microfluidics device, the negatively charged surface of the device is capable of being subjected to matrix-assisted laser desorption/ionization (MALDI) and/or surface-enhanced laser desorption/ionization (SELDI) time-of-flight (TOF) mass spectroscopy within the optical read chamber. In a twelfth illustrative microfluidics device, the device further comprises an inlet channel through which a whole blood sample may be applied, and wherein the first compartment is capable of being in fluidic communication with the inlet channel, whereby the at least one compartment is capable of receiving the whole blood sample. In a thirteenth illustrative microfluidics device, the device further comprises at least one additional compartment that is capable of being in fluidic communication with the first compartment, the second compartment, and/or the optical read chamber, and wherein the at least one additional compartment contains a wash solution.

In a first illustrative method of determining a ratio of glycated hemoglobin to total hemoglobin in a whole blood sample, the method comprises the steps of: applying a whole blood sample on an upper surface of a blood separation membrane of a microfluidics device, the blood separation membrane having a lower surface that is associated with a first waste collection material, whereby red blood cells in the whole blood sample are captured on and/or in the blood separation membrane while plasma passes through the blood separation membrane and is wicked away from the blood separation membrane and into the first waste collection material; moving a portion of the microfluidics device so that the blood separation membrane is positioned over a negatively charged surface having a second waste collection material positioned therebelow and in association therewith; applying a lysing agent to the blood separation membrane, wherein the contents of the lysed red blood cells pass through the blood separation membrane and are brought into contact with the negatively charged surface, and wherein the negatively charged surface traps hemoglobin thereon and/or therein while the other components of lysed red blood cells are wicked away from the negatively charged surface and into the second waste collection material; moving a portion of the microfluidics device so that the negatively charged surface is positioned within an optical read chamber that allows for optical interrogation of the negatively charged surface by a spectrometer; spectroscopically measuring an amount of total hemoglobin on and/or in the negatively charged surface and an amount of one of glycated hemoglobin or non-glycated hemoglobin on and/or in the negatively charged surface; and determining a ratio of glycated hemoglobin to total hemoglobin in the whole blood sample based on the spectroscopic measurements. In second illustrative method, the blood separation membrane is an asymmetric membrane vertical flow strip with larger pores on a first side and smaller pores on a second side. In a third illustrative method, negatively charged surface is spectroscopically measured by at least one of near-infrared (NIR) spectroscopy, mid-infrared (MIR) spectroscopy, and visible spectroscopy. In a fourth illustrative method, the third method further comprises the step of treating the negatively charged surface with a labeling agent capable of labeling one of glycated hemoglobin or non-glycated hemoglobin prior to positioning the negatively charged surface within the optical read chamber. In a fifth illustrative method, the fourth method further comprises the step of washing the negatively charged surface after application of the labeling agent thereto and while the negatively charged surface is associated with the second waste collection material. In a sixth illustrative method, the negatively charged surface of the third method is further defined as having a labeling agent associated therewith, wherein the labeling agent is capable of labeling one of glycated hemoglobin or non-glycated hemoglobin. In a sixth illustrative method, the labeling agent in any of the fourth, fifth, or sixth methods is boronate, wherein the boronate labels glycated hemoglobin trapped on and/or in the negatively charged surface. In a seventh illustrative method, the boronate of the seventh method is labeled with a NIR/MIR dye. In an eighth illustrative method, the negatively charged surface of the first method is spectroscopically measured by matrix-assisted laser desorption/ionization (MALDI) and/or surface-enhanced laser desorption/ionization (SELDI) time-of-flight (TOF) mass spectroscopy. In a ninth method, the first method further comprising one or both of the steps of: washing the blood separation membrane after applying the whole blood sample thereto and while the blood separation membrane is associated with the first waste collection material; and washing the negatively charged surface after application of the lysing agent thereto and while the negatively charged surface is associated with the second waste collection material.

In a tenth illustrative method of determining a ratio of glycated hemoglobin to total hemoglobin in a whole blood sample, the tenth method comprises the steps of: applying a whole blood sample on an upper surface of a blood separation membrane of a microfluidics device, the blood separation membrane having a lower surface that is associated with a waste collection material, whereby red blood cells in the whole blood sample are captured on and/or in the blood separation membrane while plasma passes through the blood separation membrane and is wicked away from the blood separation membrane and into the waste collection material; applying a labeling agent to the blood separation membrane, wherein the labeling agent penetrates the red blood cells and labels either glycated hemoglobin or non-glycated hemoglobin, and wherein excess labeling agent that did not penetrate the red blood cells is wicked away from the blood separation membrane and into the waste collection material; applying a wash solution to the blood separation membrane, wherein the wash solution is wicked away from the blood separation membrane and into the waste collection material; and measuring, via at least one of near-infrared (NIR) spectroscopy, mid-infrared (MIR) spectroscopy, and visible spectroscopy: (i) an amount of total hemoglobin on the blood separation membrane, and (ii) an amount of either: (a) labeled glycated hemoglobin on the blood separation membrane, or (b) labeled non-glycated hemoglobin on the blood separation membrane; and determining a ratio of glycated hemoglobin to total hemoglobin in the whole blood sample based on the spectroscopic measurements. In an eleventh illustrative method, the blood separation membrane of the tenth method is an asymmetric membrane vertical flow strip with larger pores on a first side and smaller pores on a second side. In a twelfth illustrative embodiment, the labeling agent of the tenth method is boronate, wherein the boronate labels glycated hemoglobin on and/or in the blood separation membrane. In a thirteenth illustrative embodiment, the boronate of the twelfth method is labeled with a NIR/MIR dye.

What is claimed is:

1. A microfluidics device for determining a ratio of glycated hemoglobin to total hemoglobin, the microfluidics device comprising:
    a first compartment configured to receive a whole blood sample, the first compartment comprising a blood separation membrane and a waste collection material positioned therebelow and associated therewith, wherein the blood separation membrane traps red blood cells thereon and/or therein, and wherein plasma passes through the blood separation membrane and is wicked away from the blood separation membrane and into the waste collection material;
    a second compartment comprising a negatively charged surface and a waste collection material positioned therebelow and associated therewith, wherein the negatively charged surface traps hemoglobin thereon and/or therein, and wherein other components of lysed red blood cells are not trapped on the negatively charged surface and are wicked away from the negatively charged surface and into the waste collection material, and wherein the negatively charged surface is configured for subjection to spectroscopy to measure an amount of total hemoglobin trapped thereon and/or therein and an amount of glycated hemoglobin or non-glycated hemoglobin trapped thereon and/or therein; and
    an optical read chamber configured for optical interrogation by a spectrometer;
    wherein the blood separation membrane is configured for releasable movement from association with the waste collection material to association with the negatively charged surface in the second compartment;
    wherein the negatively charged surface is configured for releasable movement from association with the blood separation membrane to a position within the optical read chamber, and wherein the negatively charged surface can be subjected to spectroscopy within the optical read chamber for measuring (1) an amount of total hemoglobin present on the negatively charged surface, and (2) an amount of one of glycated hemoglobin or non-glycated hemoglobin present on the negatively charged surface; and
    wherein a labeling agent is associated with or applied to one of the blood separation membrane and the negatively charged surface, wherein the labeling agent is configured to label one of glycated hemoglobin or non-glycated hemoglobin for measurement thereof.

2. The microfluidics device of claim 1, further comprising:
    a first actuator for releasably moving the blood separation membrane from association with the waste collection material to association with the negatively charged surface in the second compartment; and
    a second actuator for releasably moving the negatively charged surface from association with the blood separation membrane and the waste collection material to a position within the optical read chamber.

3. The microfluidics device of claim 1, wherein the negatively charged surface is configured for subjection to at least one of near-infrared (NIR) spectroscopy, mid-infrared (MIR) spectroscopy, and visible spectroscopy within the optical read chamber.

4. The microfluidics device of claim 3, wherein the labeling agent comprises boronate, wherein the boronate labels one of glycated hemoglobin or non-glycated hemoglobin on and/or in the negatively charged surface, wherein the boronate is labeled with a NIR/MIR dye.

5. A method of determining a ratio of glycated hemoglobin to total hemoglobin in a whole blood sample, the method comprising the steps of:
    applying a whole blood sample on an upper surface of a blood separation membrane of a microfluidics device, the blood separation membrane having a lower surface that is associated with a first waste collection material, whereby red blood cells in the whole blood sample are captured on and/or in the blood separation membrane while plasma passes through the blood separation membrane and is wicked away from the blood separation membrane and into the first waste collection material;
    moving a portion of the microfluidics device so that the blood separation membrane is positioned over a negatively charged surface having a second waste collection material positioned therebelow and in association therewith;
    applying a lysing agent to the blood separation membrane to lyse the red blood cells captured on and/or in the blood separation membrane and form lysed red blood cells, wherein the lysed red blood cells pass through the blood separation membrane and are brought into contact with the negatively charged surface, and wherein the negatively charged surface traps hemoglobin thereon and/or therein while other components of the lysed red blood cells are wicked away from the negatively charged surface and into the second waste collection material, wherein a labeling agent is associated with or applied to one of the blood separation membrane and the negatively charged surface, wherein the labeling agent is configured to label one of glycated hemoglobin or non-glycated hemoglobin for measurement thereof;

moving a portion of the microfluidics device so that the negatively charged surface is positioned within an optical read chamber that allows for optical interrogation of the negatively charged surface by a spectrometer;

spectroscopically measuring an amount of total hemoglobin on and/or in the negatively charged surface and an amount of one of glycated hemoglobin or non-glycated hemoglobin on and/or in the negatively charged surface; and determining a ratio of glycated hemoglobin to total hemoglobin in the whole blood sample based on the spectroscopic measurements.

6. The method of claim 5, wherein the negatively charged surface is spectroscopically measured by at least one of near-infrared (NIR) spectroscopy, mid-infrared (MIR) spectroscopy, and visible spectroscopy.

7. The method of claim 5, wherein the labeling agent is boronate, wherein the boronate labels glycated hemoglobin trapped on and/or in the negatively charged surface, wherein the boronate is labeled with a NIR/MIR dye.

* * * * *